United States Patent [19]

Anderson et al.

[11] Patent Number: 4,495,346

[45] Date of Patent: Jan. 22, 1985

[54] METHOD OF PREPARING A DISACCHARIDE

[75] Inventors: Laurens Anderson, Madison, Wis.; Mina A. Nashed, Alexandria, Egypt

[73] Assignee: Wisconsin Alumni Research Foundation, Madison, Wis.

[21] Appl. No.: 433,055

[22] Filed: Oct. 6, 1982

Related U.S. Application Data

[63] Continuation-in-part of Ser. No. 248,692, Mar. 30, 1981, abandoned.

[51] Int. Cl.$^3$ .............................................. C07H 1/00
[52] U.S. Cl. .................... 536/18.5; 536/4.1; 536/17.2; 536/53; 536/119; 536/124
[58] Field of Search ............... 536/4.1, 17.2, 53, 119, 536/18.5, 124

[56] References Cited

U.S. PATENT DOCUMENTS

| | | | |
|---|---|---|---|
| 2,922,783 | 1/1960 | Kuhn et al. | 536/18 |
| 3,023,183 | 2/1962 | Nelson | 536/118 |
| 3,158,598 | 11/1964 | Morel | 536/18 |
| 4,152,513 | 5/1979 | Austin et al. | 536/4 |

OTHER PUBLICATIONS

Kiso et al., "Carbohydrate Research", 81, 1980, pp. C13–C15.

Inage et al., "Tetrahedron Letter", 21, 1980, pp. 3889–3892.

Nashed et al., "Abstracts Papers", 181st ACS National Meeting, CARB 28, 1980.

Kiso et al., "Carbohydrate Research", 88, 1981, pp. C10–C13.

*Primary Examiner*—Johnnie R. Brown
*Attorney, Agent, or Firm*—Quarles & Brady

[57] ABSTRACT

Novel disaccharides useful in preparing analogs of lipid A are prepared by first preparing novel precursors of the reducing and non-reducing moieties of the lipid A molecule and then catalytically coupling the precursors.

4 Claims, 4 Drawing Figures

METHOD OF PREPARING A DISACCHARIDE

This invention was made with Government support under NIH Grant No. AM-10588 awarded by the Department of Health and Human Services. The Government has certain rights in this invention.

RELATED CASE

This application is a continuation-in-part of our earlier U.S. patent application Ser. No. 248,692 filed Mar. 30, 1981, now abandoned.

FIELD OF THE INVENTION

The present invention relates to novel analogs of enterobacterial lipid A, methods of synthesizing such analogs and lipid A and novel precursors useful in such methods.

DESCRIPTION OF THE PRIOR ART

The lipid A of Salmonella species and *E. coli* which is a component of the bacterial lipopolysaccharide is of biochemical and pharmacological interest, because it is responsible for the endotoxic and other potent biological activities of the lipopolysaccharides from which it is derived. Thus, compounds of the lipid A group are attractive goals for synthetic efforts. "Building blocks" for the lipid A molecule have been described by M. Kiso et al, *Carbohydr. Res.* 81 (1980) C13-C15. More recently, Inage et al in *Tetrahedron Lett.*, 21 (1980) 3889–3892 and *Chem. Lett.* (1980) 1373–1376 and Kiso et al, *Carbohydr. Res.*, 88 (1981) C10–C13, have described the synthesis of derivatives of the disaccharide β-D-GlcpN(1→6)D-GlcpN having fatty acyl groups at all of the same positions as the natural lipid, or on the nitrogen atoms. These derivatives were made from glycosides of the disaccharide by a complicated series of deblocking, blocking, and acylation steps.

A need still exists for a relatively simple method of synthesizing analogs of lipid A and lipid A itself.

SUMMARY OF THE PRESENT INVENTION

The present invention relates to novel analogs of lipid A of the following formula:

in which R is an alkyl, hydroxyalkyl or protected hydroxyalkyl of 7 to 19 carbon atoms, preferably an alkyl of 15 carbon atoms and in which the hydroxy group is protected as an ether, an acetal or ketal, or an ester such as methyl ether, t-butyl ether, allyl ether, benzyl ether, trityl ether, substituted trityl ethers, tetrahydropyranyl ether, acetate, benzoate, formate, trifluoro-, chloro-, methoxy- and phenoxy acetates and the like; $R_1$ is hydrogen, a phosphoryl of the formula in which $R_7$ and $R_8$ are the same or different and are phenyl, benzyl, 2-cyanoethyl, 2,2,2-trichlorethyl, methyl or $R_7$ and $R_8$ is o-phenylene; $-OPO_3=M_2^+$ in which $M^+$ is a cation which forms a salt with deblocked phosphate groups such as $Na^+$, $K^+$, $Zn^{++}$, $NH_4^+$ or a substituted ammonium ion such as cyclohexylammonium, tri-n-butylammonium or tetraethylammonium or the like; or a group which can be removed selectively under fairly mild conditions without adverse effects in the presence of ester, benzyl ether and phosphorylated groups such as allyl, 1-propenyl or 2,2,2-trichloroethyl; $R_3'$ is a group which can be removed selectively under fairly mild conditions such as allyl, crotyl, 2-methoxyethoxymethyl, methylthiomethyl and benzyl which includes substituted benzyls such as lower alkyl benzyl in which the lower alkyl is 1 to 4 carbons such as methylbenzyl; $R_4'$ is hydrogen;

in which $R_7$ and $R_8$ are the same or different and are phenyl, benzyl, 2-cyanoethyl, 2,2,2,-trichloroethyl, methyl or $R_7$ and $R_8$ is o-phenylene; $-OPO=3\ M_2^+$ in which $M^+$ is a cation which forms a salt with deblocked phosphate groups such as $Na^+$, $K^+$, $Zn^{++}$, $NH_4^+$ or a substituted ammonium ion such as cyclohexylammonium, tri-n-butylammonium or tetraethylammonium or the like; or a group which can be removed under neutral conditions without adverse effects in the presence of esters, such as chloroacetyl, β-benzoylpropionyl or levulinyl and $R_4$ is hydrogen or In the method of the present invention the novel compounds of Formula I are prepared by first preparing precursors of the non-reducing and reducing moieties of lipid A, respectively, having their fatty acyl groups in place and then coupling the precursors to form novel disaccharide derivatives which by phosphorylation and deblocking can be converted into lipid A and its analogs.

The coupling reaction may be illustrated as follows:

-continued in which R is as previously described, $R_1$ is preferably allyl, benzyl or 2,2,2-trichloroethyl, $R_3'$ is preferably allyl, crotyl, 2-methoxyethoxymethyl or benzyl, $R_4'$ is preferably in which $R_7$ and $R_8$ are both trichloroethyl, chloroacetyl, β-benzoylpropionyl or levulinyl and $R_4$ is hydrogen.

The disaccharide, Compound IV can be converted by use of conventional techniques to obtain lipid A analogs.

It will be apparent to those skilled in the art that our novel synthetic method has the usual advantages of convergent schemes, and that it exploits structural elements (fatty acyl groups) of the target compounds as protecting groups, thus minimizing the use of temporary protecting groups.

DESCRIPTION OF THE PREFERRED EMBODIMENT

In the practice of the method of the present invention disaccharides of Formula I are prepared by first preparing precursors of the non-reducing and reducing moieties of lipid A as represented herein by Formulas II and III, respectively from allyl and benzyl 3,4,6-tri-O-acetyl-2-acylamido-2-deoxy-β-D-glucopyranosides and then coupling them to form the disaccharide of Formula IV.

Figure 1:
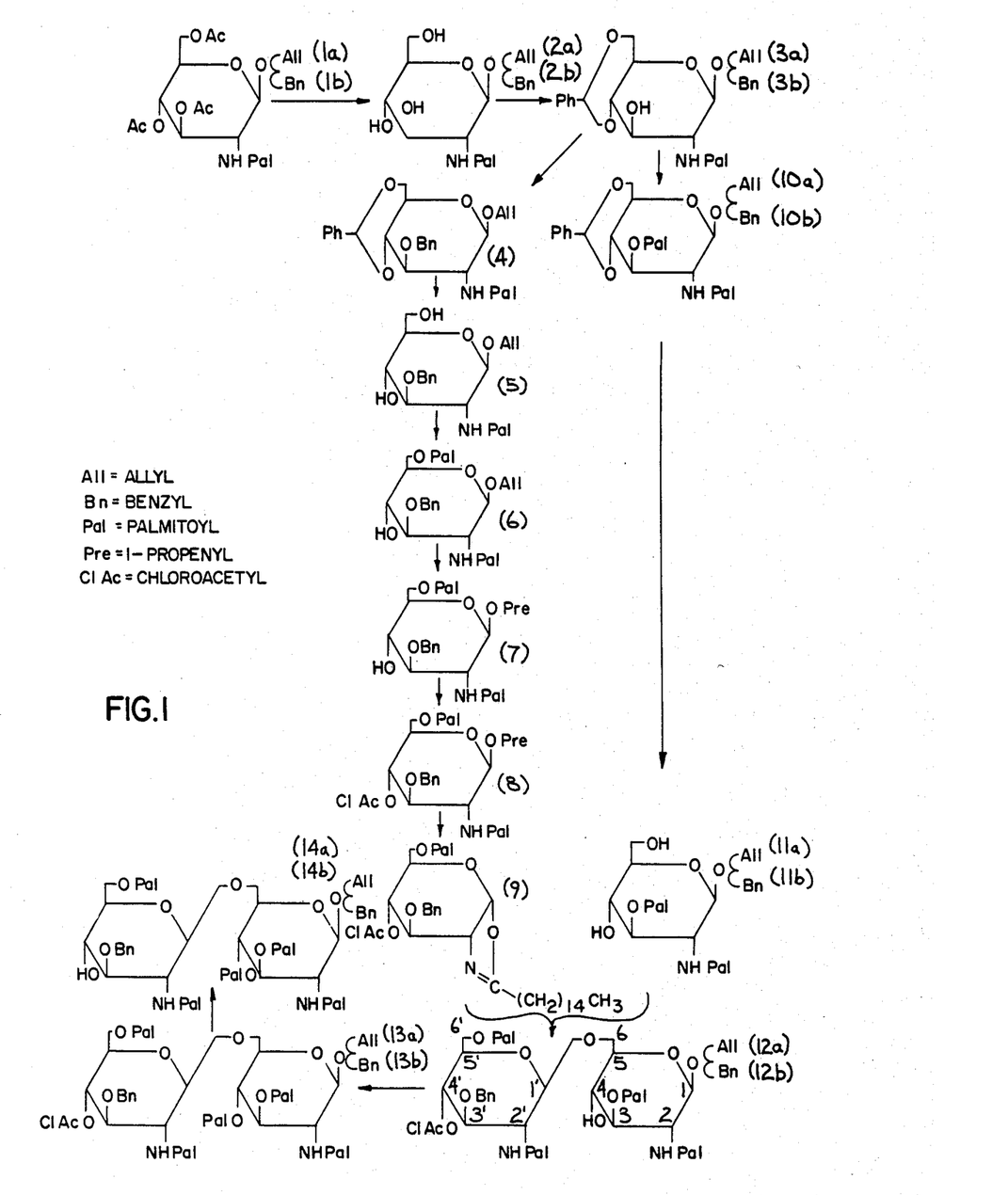
FIG. 1 of the drawing is a flow sheet showing the preferred method of preparation of the lipid A analogs from allyl and benzyl 3,4,6-tri-O-acetyl-2-deoxy-2-palmitamido-β-D-glucopyranoside.

The stepwise preparation of the precursors and the disaccharide of Formula IV is illustrated in FIG. 1 of the drawing. As illustrated therein, the allyl (Compound 1a) and benzyl (Compound 1b) 3,4,6-tri-O-acetyl-2-deoxy-2-palmitamido-β-D-glucopyranosides are de-O-acetylated, preferably using sodium methoxide in methanol, to yield allyl 2-deoxy-2-palmitamido-β-D-glucopyranoside (Compound 2a) and benzyl 2-deoxy-2-palmitamido-β-D-glucopyranoside (Compound 2b), respectively. Treatment of the glycosides (Compound 2a and Compound 2b) with benzaldehyde and zinc chloride in the manner described by D. M. Hall in Carbohydr. Res., 86 (1980) 158–160 yields the key, crystalline intermediates allyl 4,6-O-benzylidene-2-deoxy-2-palmitamido-β-D-glucopyranoside (Compound 3a) and benzyl 4,6-O-benzylidene-2-deoxy-2-palmitamido-β-D-glucopyranoside (Compound 3b).

The allyl derivative (Compound 3a) is then used to prepare the precursor (Compound 9) for the non-reducing half of the target disaccharides which must be an activated derivative of 2-deoxy-2-palmitamido-D-glucose carrying an O-palmitoyl group at position 6 and protecting groups at positions 3 (unsubstituted in lipid A) and 4 (phosphorylated in lipid A). The oxazoline (compound 9 in FIG. 1) may be obtained from compound 3a via intermediates 4–8 of FIG. 1. The benzylation of compound 3a with benzyl bromide, barium oxide, and barium hydroxide in N,N-dimethylformamide in the manner described by R. Harrison and H. G. Fletcher, Jr., J. Org. Chem., 30 (1965) 2317–2321 furnishes allyl 3-O-benzyl-4,6-O-benzylidene-2-deoxy-2-palmitamido-β-D-glucopyranoside (Compound 4). On boiling with 80% aqueous acetic acid, it is quickly hydrolyzed to allyl 3-O-benzyl-2-deoxy-2-palmitamido-β-D-glucopyranoside (Compound 5). The acylation of the primary hydroxyl is accomplished by treating Compound 5 with 1.2 molar portions of palmitoyl chloride, which gives allyl 3-O-benzyl-2-deoxy-2-palmitamido-6-O-palmitoyl-β-D-glucopyranoside (Compound 6) in high yield.

Next, the rearrangement of the glycosidic allyl group in Compound 6 is catalyzed by tris(triphenylphosphine)rhodium(I) chloride in the manner described by E. J. Corey and J. W. Suggs, J. Org. Chem., 38 (1973) 3224 and P. A. Gent and R. Gigg, J. Chem. Soc., Chem. Commun., (1974) 277–278 to provide 1-propenyl 3-O-benzyl-2-deoxy-2-palmitamido-6-O-palmitoyl-β-D-glucopyranoside (Compound 7). The fully substituted glycoside, 1-propenyl 3-O-benzyl-4-O-chloroacetyl-2-deoxy-2-palmitamido-6-O-palmitoyl-β-D-glucopyranoside (Compound 8), is then generated by the reaction of Compound 7 with chloroacetyl chloride. Cyclization, by the procedure developed and described by M. A. Nashed et al, Carbohydr. Res., 82 (1980) 237–252 employing mercuric chloride, mercuric oxide and acetonitrile is used to convert Compound 8 into 2-pentadecyl-(3-O-benzyl-4-O-chloroacetyl-1,2-dideoxy-6-O-palmitoyl-α-D-glucopyrano)[2,1-d]-2-oxazoline (Compound 9) a compound of Formula II.

The synthesis of the precursor compounds of Formula III involves first the acylation of the compound 3a, where $R_1$ is allyl, and Compound 3b, where $R_1$ is benzyl, with palmitoyl chloride, which gives allyl 4,6-O-benzylidene-2-deoxy-2-palmitamido-3-O-palmitoyl-β-D-glucopyranoside (Compound 10a) and benzyl 4,6-O-benzylidene-2-deoxy-2-palmitamido-3-O-palmitoyl-β-D-glucopyranoside (Compound 10b), respectively. The Compounds 10a and 10b when briefly heated in 80% aqueous acetic acid give the desired allyl 2-deoxy-2-palmitamido-3-O-palmitoyl-β-D-glucopyranoside (Compound 11a) and benzyl 2-deoxy-2-palmitamido-3-O-palmitoyl-β-D-glucopyranoside (Compound 11b), respectively.

The coupling of an oxazoline precursor of Formula II with a precursor of Formula III is preferably conducted in the manner described by M. A. Nashed et al in *Carbohydr. Res.*, 90 (1981) 71–82 employing p-toluenesulfonic acid in 1,2-dichloroethane to obtain the desired analogs of lipid A, the disaccharides of Formula IV (Compounds 12a and 12b) in good yields.

The allyl and benzyl 3,4,6-tri-O-acetyl-2-deoxy-2-palmitamido-β-D-glucopyranosides (Compounds 1a and 1b) which are employed as starting materials are known compounds which may be prepared from 1,3,4,6-tetra-O-acetyl-2-amino-2-deoxy-β-D-glucopyranose hydrochloride as described by Kiso et al in *Carbohydr. Res.*, 81 (1980) C13–C15.

Figure 2:
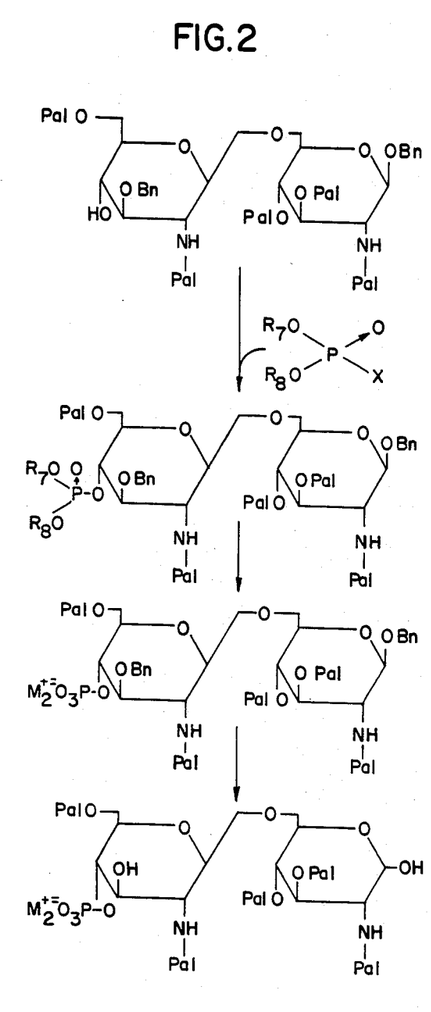
FIG. 2 is a flow sheet showing a synthetic route from the disaccharide 14b of FIG. 1 to an analog of 1-dephospho lipid A.
Figure 3:
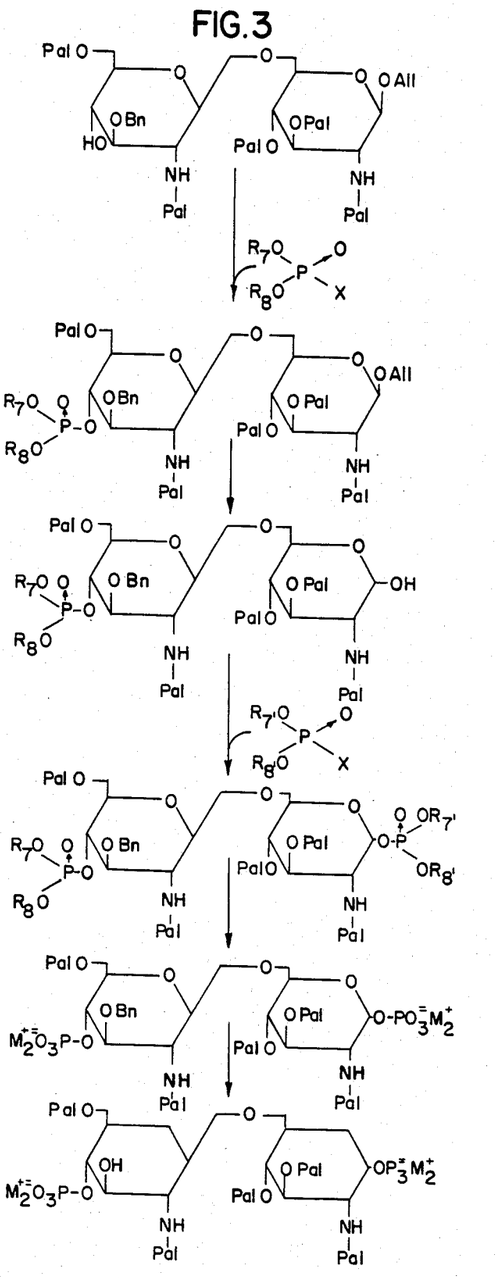
FIG. 3 is a flow sheet showing a synthetic route from the disaccharide 14a of FIG. 1 to a complete analog of lipid A.

Two synthetic routes by which additional analogs of lipid A may be prepared from the disaccharides 14a and 14b are illustrated in FIGS. 2 and 3 of the drawing.

The following examples further illustrate the practice of the method of the present invention.

EXAMPLE 1

Allyl 2-deoxy-2-palmitamido-β-D-glucopyranoside (Compound 2a)

A solution of 6 grams of allyl 3,4,6-tri-O-acetyl-2-deoxy-2-palmitamido-β-D-glucopyranoside (Compound 1a) in 150 ml. of methanol was refluxed for about 30 minutes after the addition of a piece of sodium metal. A sulfonic cation exchange resin was added to remove the sodium, followed by hot filtration. The filtrate was concentrated on a hot plate and stored overnight in a freezer. It was then filtered to yield the desired compound as a gelatinous solid.

EXAMPLE 2

Benzyl 2-deoxy-2-palmitamido-β-D-glucopyranoside (Compound 2b)

A solution of 5 grams of benzyl 3,4,6-tri-O-acetyl-2-deoxy-2-palmitamido-β-D-glucopyranoside (Compound 1b) in 140 ml. of methanol was refluxed for about 30 minutes after the addition of a piece of sodium metal. A sulfonic cation exchange resin was added to remove the sodium, followed by hot filtration. The filtrate was concentrated on a rotary evaporator to yield the desired product in the form of a gelatinous solid which was stored in an evacuated oven at 70° C. overnight.

EXAMPLE 3

Allyl 4,6-O-benzylidene-2-deoxy-2-palmitamido-β-D-glucopyranoside (Compound 3a)

To a mixture of benzaldehyde (15 ml.) and zinc chloride (4 g.) which was stirred for about 30 minutes was added 4 g. of the Compound 2a of Example 1. The reaction mixture was stirred for about 3 hours at room temperature at which time t.l.c. (thin layer chromatography) with 15% methanol in chloroform showed complete reaction. The reaction mixture was poured into 100 ml. of water containing 5 g. of $NH_4Cl$ and 100 ml. of Skellysolve B. The precipitate was filtered off, suspended in hot methanol with stirring, then left to cool to room temperature and filtered. The desired Compound 3a was then crystallized from ethanol.

EXAMPLE 4

Benzyl 4,6-O-benzylidene-2-deoxy-2-palmitamido-β-D-glucopyranoside (Compound 3b)

The procedure described in Example 3 was repeated using the compound of Example 2, Compound 2b, as the starting material to obtain the desired Compound 3b.

EXAMPLE 5

Allyl 3-O-benzyl-4,6-O-benzylidene-2-deoxy-2-palmitamido-β-D-glucopyranoside (Compound 4) and allyl 3-O-benzyl-2-deoxy-2-palmitamido-β-D-glucopyranoside (Compound 5).

To 2 g. of allyl 4,6-O-benzylidene-2-deoxy-2-palmitamido-β-D-glucopyranoside (Compound 3a) in 40 ml. of DMF (dissolved by heating, then cooling to room temperature) was added 4 g. of BaO, 1.2 g. of Ba(OH)$_2$.8H$_2$O, and 1.3 ml. of benzyl bromide. The reaction mixture was stirred at room temperature for about 3 hours. Thin layer chromatography (2% methanol in chloroform) showed complete reaction. The mixture was then diluted with CHCl$_3$, filtered and the filter cake washed with CHCl$_3$, then the CHCl$_3$ was washed with HCl, dried and evaporated. The residue was chromatographed on silica gel using 2% methanol in chloroform to obtain the desired Compound 4.

Upon boiling with 80% aqueous acetic acid for 30 minutes the allyl 3-O-benzyl-4,6-O-benzylidene-2-deoxy-2-palmitamido-β-D-glucopyranoside (Compound 4) was quickly hydrolyzed to allyl 3-O-benzyl-2-deoxy-2-palmitamido-β-D-glucopyranoside (Compound 5) in high yield.

EXAMPLE 6

Allyl 3-O-benzyl-2-deoxy-2-palmitamido-6-O-palmitoyl-β-D-glucopyranoside (Compound 6).

To 0.38 g. of allyl 3-O-benzyl-2-deoxy-2-palmitamido-β-D-glucopyranoside (Compound 5) in 7 ml. dry pyridine at about 15° C., was added 0.3 ml. of palmitoyl chloride. After warming and holding at room temperature for 4 hours, thin layer chromatography (5% methanol in chloroform) showed the reaction to be complete. Methanol was then added and the solvent evaporated and coevaporated with toluene. Column chromatography of the residue (5% acetone in CHCl$_3$) yielded Compound 6.

EXAMPLE 7

1-Propenyl 3-O-benzyl-2-deoxy-2-palmitamido-6-O-palmitoyl-β-D-glucopyranoside (Compound 7)

To 500 mg. of Compound 6 in a mixture of 2.0 ml. of ethanol, benzene and water (7:3:1) 40 mg. of tris(triphenylphosphine)rhodium(I) chloride and 15 mg. of 1,4-diazabicyclo-[2.2.2]octane were added. The reaction mixture was heated under reflux overnight. Thin layer chromatography (5% acetone in CHCl$_3$) showed the reaction to be complete. The reaction was conducted in the general manner described by Corey et al, in *J. Org. Chem.*, 38 (1973) 3224 and P. A. Gent et al, *J. Chem. Soc., Chem. Commun.*, (1974) 277–278. A high yield of Compound 7 was obtained.

EXAMPLE 8

1-Propenyl 3-O-benzyl-4-O-chloroacetyl-2-deoxy-2-palmitamido-6-O-palmitoyl-β-D-glucopyranoside (Compound 8)

To 0.4 g. of Compound 7 in 15 ml. of $CH_2Cl_2$ was added 0.4 ml. of pyridine. The reaction mixture was cooled to about 0° C. and 0.4 ml. chloroacetyl chloride in 5 ml. of $CH_2Cl_2$ was added dropwise with stirring. After stirring at room temperature for 30 minutes, thin layer chromatography showed the reaction was complete. Next water was added, then 5% HCl followed by a wash with water and $NaHCO_3$. The dried chloroform layer was evaporated and the residue taken up in hot methanol and the solid material filtered off. Thin layer chromatography showed the solid material to be Compound 8 of high purity.

EXAMPLE 9

2-Pentadecyl-(3-O-benzyl-4-O-chloroacetyl-1,2-dideoxy-6-O-palmitoyl-α-D-glucopyrano)-[2,1-d]-2-oxazoline (Compound 9)

To 240 mg. of Compound 8 in 5 ml. of $CH_3CN$ at 80° C. were added 60 mg. of HgO and 114 mg. of $HgCl_2$. The reaction mixture was refluxed for 1 hour at which time thin layer chromatography (5% acetone in chloroform) showed the reaction to be complete. A high yield of the desired Compound 9 was obtained.

Compound 9 is the oxazoline that is used as the precursor (Formula II) for the non-reducing half of the disaccharide of Formula IV.

Examples 10 and 11 relate to the preparation of the precursors of Formula III (Compounds 11a and 11b).

EXAMPLE 10

Allyl 4,6-O-benzylidene-2-deoxy-2-palmitamido-3-O-palmitoyl-β-D-glucopyranoside (Compound 10a) and Allyl 2-deoxy-2-palmitamido-3-O-palmitoyl-β-D-glucopyranoside (Compound 11a).

To 2 g. of Compound 3a, prepared as described in Example 3, in 100 ml. of pyridine was added 2 ml. (2 molar equivalents) of palmitoyl chloride. The reaction mixture was stirred at room temperature for about 3 hours to yield the desired Compound 10a.

The Compound 10a thus obtained was de-O-benzylidenated by heating in 80% aqueous acetic acid at reflux for about 20 minutes to yield the Compound 11a.

EXAMPLE 11

Benzyl 4,6-O-benzylidene-2-deoxy-2-palmitamido-3-O-palmitoyl-β-D-glucopyranoside (Compound 10b) and Benzyl 2-deoxy-2-palmitamido-3-O-palmitoyl-β-D-glucopyranoside (Compound 11b)

The procedure of Example 10 was repeated using Compound 3b as the starting material to prepare Compounds 10b and 11b.

EXAMPLE 12

Allyl O-(3-O-benzyl-4-O-chloroacetyl-2-deoxy-2-palmitamido-6-O-palmitoyl-β-D-glucopyranosyl)-(1→6)-2-deoxy-2-palmitamido-3-O-palmitoyl-β-D-glucopyranoside (Compound 12a)

To a solution of Compound 11a (200 mg., 0.29 mmol.) and p-toluenesulfonic acid (8-10 mg.) in 1,2-dichloroethane (3 ml.), the oxazoline derivative Compound 9 (430 mg., 2 molar portions) was added and the reaction mixture was stirred for 8 h. at 65°-70° under rigorously anhydrous conditions. The cooled reaction mixture was diluted with chloroform and washed with 5% sodium hydrogencarbonate, then water and dried with magnesium sulfate. The syrup obtained by evaporation of the solvents was purified on a column of silica gel. The yield of Compound 12a was 230 mg. (53%), amorphous solid $[\alpha]_D^{25} -1.6°$, $[\alpha]_{436}^{25} -2.7°$ (c 0.78, chloroform).

EXAMPLE 13

Benzyl O-(3-O-benzyl-4-O-chloroacetyl-2-deoxy-2-palmitamido-6-O-palmitoyl-β-D-glucopyranosyl)-(1→6)-2-deoxy-2-palmitamido-3-O-palmitoyl-β-D-glucopyranoside (Compound 12b)

The procedure of Example 12 was repeated using Compound 11b as the starting material to obtain Compound 12b.

EXAMPLE 14

Allyl O-(3-O-benzyl-4-O-chloroacetyl-2-deoxy-2-palmitamido-6-O-palmitoyl-β-D-glucopyranosyl)-(1→6)-2-deoxy-2-palmitamido-3,4-di-O-palmitoyl-β-D-glucopyranoside (Compound 13a)

Compound 12 (100 mg., 67 μmol.) was dissolved in dry pyridine (1.5 ml.) and the solution was cooled to 5°. Palmitoyl chloride (0.06 ml., ~3 molar portions) was added with stirring, then the mixture was allowed to warm to room temperature. After 2 hours a few drops of water were added, the solution was diluted with chloroform, and the chloroform solution was washed successively with 5% hydrochloric acid, water, 5% sodium hydrogencarbonate, and water, and then dried with anhydrous magnesium sulfate. After purification on a column of silica gel, the yield was 85-90% of the title compound 13a, amorphous solid.

EXAMPLE 15

Benzyl O-(3-O-benzyl-4-O-chloroacetyl-2-deoxy-2-palmitamido-6-O-palmitoyl-β-D-glucopyranosyl)-(1→6)-2-deoxy-2-palmitamido-3,4-di-O-palmitoyl-β-D-glucopyranoside (Compound 13b)

The procedure of Example 14 was repeated using Compound 2b as the starting material to obtain Compound 13b.

EXAMPLE 16 Allyl O-(3-O-benzyl-2-deoxy-2-palmitamido-6-O-palmitoyl-β-D-glucopyranosyl)-(1→6)-2-deoxy-2-palmitamido-3,4-di-O-palmitoyl-β-D-glucopyranoside (Compound 14a)

To a solution of Compound 13a (20 mg., 11.5 μmol) in 1:1 (v/v) chloroform-methanol (1 ml.), thiourea (5-10 mg.) was added. The reaction mixture was stirred for overnight at room temperature then diluted with chloroform (1.5 ml.) and the solid material was removed by filtration. The solvents were evaporated and the residue obtained was purified on a column of silica gel to yield 75–80% of the pure Compound 14a, $[\alpha]_D^{25} -7.6°$, $[\alpha]_{436}^{25} -18.4°$ (c 0.3, chloroform).

EXAMPLE 17

Benzyl O-(3-O-benzyl-2-deoxy-2-palmitamido-6-O-palmitoyl-β-D-glucopyranosyl)-(1→6)-2-deoxy-2-palmitamido-3,4-di-O-palmitoyl-β-D-glucopyranoside (Compound 14b)

The procedure of Example 16 was repeated using Compound 13b as the starting material to obtain Compound 14b.

The compounds of the foregoing Examples were purified to homogeneity (thin layer chromatography) by recrystallization, or by chromatography on columns of silica gel when necessary. All were well characterized by $^1$H-n m.r. spectroscopy, and when elemental analyses were obtained the values were within ±0.4% of the theoretical. Yields, specific rotations, melting points (for crystalline products), and selected n.m.r. data are presented in Table I.

chloroacetyl group and the phosphorylation of the 4'-position. One or two stage removal of all protecting groups from the phosphorylated benzyl glycoside yields the palmitoyl analog of 1-dephospho lipid A. In the case of the phosphorylated allyl glycoside the 1-allyl group can be selectively removed and the 1-position phosphorylated. Cleavage of the protecting groups from the doubly phosphorylated product will furnish the palmitoyl analog of lipid A.

In FIG. 2 of the drawing is illustrated a proposed route from the protected disaccharide Compound 14b to the palmitoyl analog of monodephospho lipid A. Step 1 in the proposed route is phosphorylation at position 4' with a reagent of the type where R may be phenyl, benzyl, 2-cyanoethyl, 2,2,2-trichloroethyl, etc.; or R+R is o-phenylene; and X is chloro, imidazolyl, 1,2,4-triazolyl, arylsulfonyl, etc. H. Kossel and H. Seliger, *Progr. Chem. Organic Natural Products*, 32 (1975) 297. Step 2 in the proposed route is

TABLE I

| | | | | CHARACTERIZING DATA |
|---|---|---|---|---|
| Compound[a] | Yield (%) | M.p. (°C.) | $[\alpha]_D^{25}$ (degrees)[b] | $^1$H-N.m.r. at 270 MHz[c] |
| 2a | 95 | 180–181 | −20.2 (MeOH) | (Me$_2$SO—d$_6$) No CH$_3$CO |
| 2b | 98 | amorph. | −28.2 (MeOH) | (Me$_2$SO—d$_6$) No CH$_3$CO |
| 3a* | 85 | 220–221 | −45.8 | δ 7.61–7.32 (5 Ph—H), 5.58 (s, PhCH) |
| 3b* | 90 | 225–226 | −62.6 | δ 7.61–7.32 (10 Ph—H), 5.59 (s, PhCH) |
| 4* | 94 | amorph. | −1.8 | δ 7.52–7.08 (10 Ph—H), 4.76 (AB,PhCH$_2$) |
| 5* | 80 | amorph. | −8.1 | δ 7.42–7.33 (5 Ph—H), no PhCH |
| 6* | 88 | amorph. | −10.5 | δ 3.94–3.70 (m, H—6, H—6'), 2.10 (t, J 6.5 Hz, CH$_2$CO). |
| 7 | >90 | amorph. | | δ 6.28–6.11 (m, OCH=), no OCH$_2$CH=CH$_2$ |
| 8* | 84 | 95–96 | +5.9 | δ 5.34 (m, H—4) |
| 9 | >90 | amorph. | | δ 6.01 (d, J 7.5 Hz, H—1) |
| 10a* | 95 | amorph. | −40.0 | δ 5.28 (t, J 9.0 Hz, H—3), 2.32 (t, J 6.5 Hz, CH$_2$CO) |
| 10b* | 85 | 171–172 | −56.0 | δ 5.21 (t, J 9.3 Hz, H—3), 2.15 (t, J 7.0 Hz, CH$_2$CO) |
| 11a* | 80 | amorph. | −18.7 | No Ph—H or PhCH |
| 11b* | 82 | amorph. | −30.9 | 5 Ph—H, no PhCH |
| 12a | 40–60 | amorph. | −1.6 | δ 7.44–7.32 (Ph—H), 5.80 (m, —CH=), 5.95 and 5.40 (2 d, NH); after exchange of NH and OH, δ 5.08 and 5.40 (2 t, J 8–10 Hz, H—3 and H—4') |
| 12b | 40–60 | amorph. | −6.5 | δ 5.35–5.24 (2 t, J 8–10 Hz, H—3 and H—4'), 5.77 (d, J 6.4 Hz, NH), 5.48 (d, J 6.8 Hz, NH) |
| 13a | 90 | amorph. | | δ 5.09–4.85 (3 t, J 8–10 Hz, H—3, H—4, and H—4') |
| 13b | 85 | amorph. | | δ 5.35–5.14 (3 t, J 8–10 Hz, H—3, H—4, and H—4') |
| 14a | | amorph. | −7.6 | δ 5.30, 5.03 (2 t, J 9 Hz, H—3 and H—4) |
| 14b | | amorph. | −8.4 | δ 5.15, 4.98 (2 t, J 9.0 Hz, H—3 and H—4) |

[a]An asterisk (*) indicates that analyses for C, H, and N were performed.
[b]In chloroform unless otherwise indicated.
[c]Determined in CDCl$_3$ unless otherwise indicated. Referenced to internal tetramethylsilane. The listing gives the most significant differences between the spectrum of each compound and the spectrum of its precursor, except for 12a and 12b. For these compounds signals characteristic of each of the sugar units are listed.

The foregoing examples are to be considered merely illustrative of the practice of the method of the present invention. For example, although palmitic acid was the fatty acid used in the examples the novel synthetic scheme provides for the selective introduction of any desired fatty acid at each of the five acylated positions in the disaccharides, Compounds 13a and 13b.

The arrangement of protecting groups in the two disaccharide glycosides is such as to permit their economical conversion to analogs of lipid A and 1-dephospho lipid A, respectively. In both cases, the first steps in the conversion are the selective removal of the 4'- the deblocking of the phosphate group. The reagent employed will depend on the nature of R; it may be H$_2$ plus a noble metal catalyst, ammonium hydroxide, zinc-copper couple, bromine, or other. Kossel and Seliger (supra). In the formula, M+ is a cation which forms a salt with the deblocked phosphate groups. It may be Na+, K+, Zn++, NH$_4$+, or a substituted ammonium ion such as cyclohexylammonium, tri-n-butylammonium, tetraethylammonium, etc. The final Step 3 in the proposed route involves the removal of the benzyl protecting groups from positions 1 and 3'. It can be done by hydrogenolysis with H$_2$ over palladium-charcoal catalyst. C. B. Reese in J. F. W. McOmie, ed., "Protective Groups in Organic Chemistry," Plenum Press, New York, 1976, p. 98.

A proposed route from the protected disaccharide Compound 14a to the complete (palmitoyl) analog of natural lipid A is shown in FIG. 3 of the drawing. Step 1 in the proposed route is phosphorylation at position 4' which is accomplished as in Step 1 of the scheme of FIG. 2. Step 2 in the proposed route is the removal of the allyl group from position 1 by treatment first with tris(triphenylphosphine)rhodium(I) chloride (Wilkinson's catalyst), then with mercuric chloridemercuric oxide in acetone or other organic solvent containing a little water. Wilkinson's catalyst isomerizes the O-allyl group to a 1-propenyl group ($-O-CH_2-CH=CH_2 \rightarrow -O-CH=CH-CH_3$); the mercuric salts catalyze the hydrolysis of the resulting 1-propenyl glycoside. E. J. Corey and J. W. Suggs, *J. Org. Chem.*, 38 (1973) 3224 and P. A. Gent and R. Gigg, *J. Chem. Soc., Chem. Commun.*, (1974) 277. Step 3 is phosphorylation at position 1. The phosphorylating agent may be the same as the one used in step 1, or different. Hence the substituents in the reagent in FIG. 3 have been designated R'. Step 4 is the deblocking of the phosphate groups in the same manner as Step 2 in the scheme of FIG. 2. If R and R' are different, two deblocking reagents may have to be used in succession. The symbol M+, used in the formula of the deblocked product is the same as M+ in the scheme of FIG. 2. Step 5, the final step, is the removal of the benzyl protecting group from position 3' which is done in the same manner as Step 3, of the scheme of FIG. 2.

Alternative possibilities for the phosphorylation of position 1 would be to alter step 2 in the scheme of FIG. 3 by conducting the reaction of the 1-propenyl glycoside with mercuric chloride-mercuric oxide in anhydrous acetonitrile to give the disaccharide oxazoline (M. A. Nashed, M. Kiso, C. W. Slife, and L. Anderson, *Carbohydr. Res.*, 82 (1980) (237), then to treat the oxazoline with dibenzyl or diphenyl phosphoric acid in boiling 1,2-dichlorethane, benzene, toluene, or other suitable solvent to obtain a protected bis-phosphate. This would be the same product as expected from step 3, with R'= benzyl or phenyl. (A. Ya. Khorlin, S. E. Zurabyan, and T. S. Antonenko, *Tetrahedron Lett.*, (1970) 4803; C. D. Warren, A. Herscovics, and R. W. Jeanloz, *Carbohydr. Res.*, 61 (1978) 181.)

In another embodiment of the invention the synthesis described above has been modified by introducing a substituted phosphate group into the 4' position of the precursor of the non-reducing half of the lipid A molecule before the two halves are coupled. This eliminates the need of employing and later removing a protective group in the 4' position; thus, two steps have been saved.

The major change in the modified procedure begins with the propenyl glycoside 7. In the synthesis seen in FIG. 1, this compound was chloroacetylated to give Compound 8. The chloroacetyl group then served as a temporary protecting group during the coupling of the two halves (Compound 9+Compound 11b to yield Compound 12b), and the final palmitoylation at position 4 to yield Compound 13b. Removal of the chloroacetyl group from Compound 13b gives Compound 14b, which is then ready for the attachment of the first phosphate group (14b to 15b).

Figure 4:
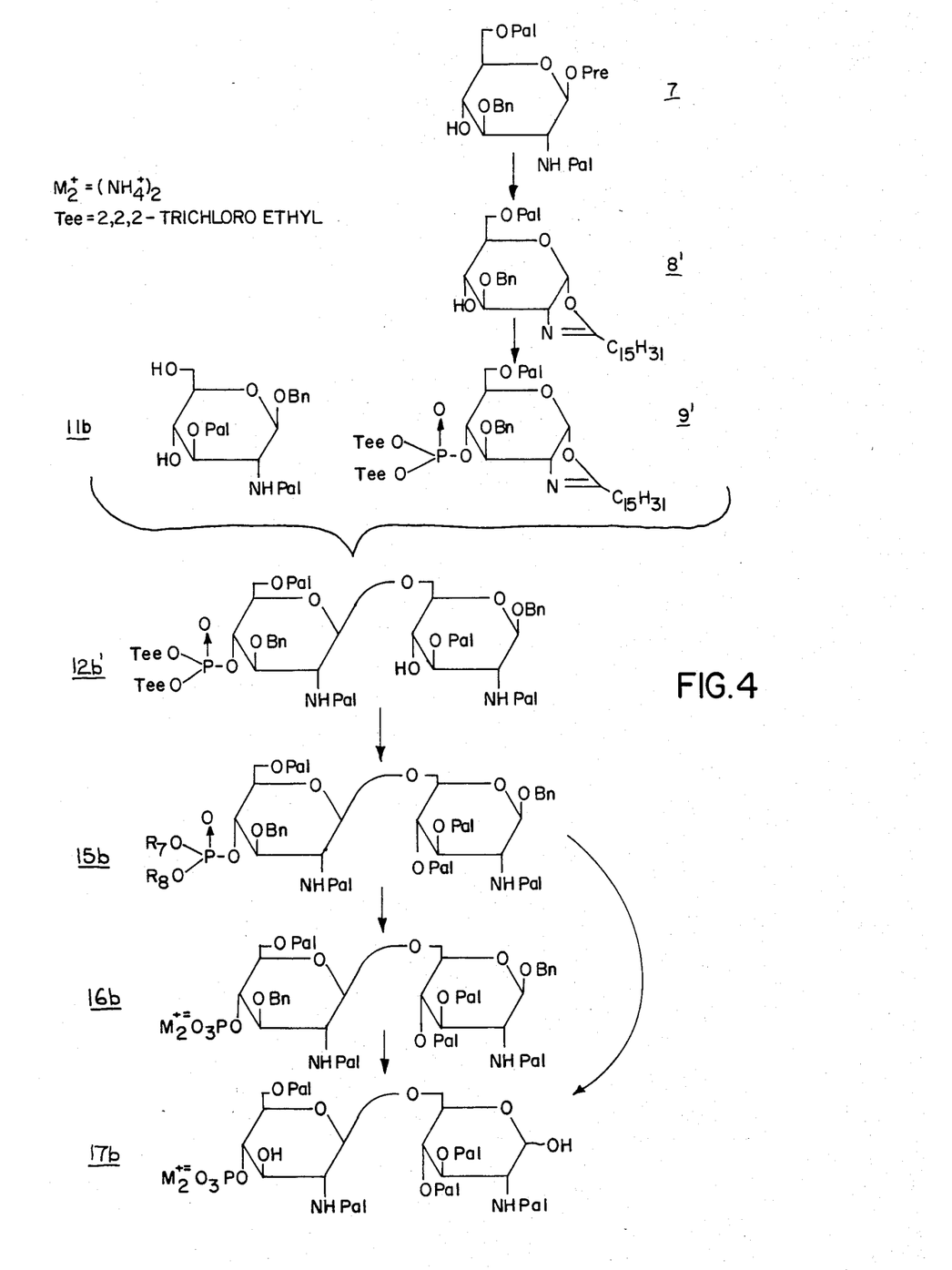
FIG. 4 is a flow sheet showing an alternate synthetic route from the propenyl glycoside 7 of FIG. 1 to a phosphorylated analog of lipid A.

In the procedure shown in FIG. 4, the propenyl glycoside 7 is directly converted to Compound 8'. The cyclization of Compound 7 is accomplished by the procedure developed and described by M. A. Nashed et al., *Carbohydr. Res.*, 82 (1980) 237–252, employing mercuric chloride and mercuric oxide as reagents and acetonitrile as the reaction medium. Alternatively, Compound 7 in dry tetrahydrofuran is treated with 1.5 molar portions of iodine and 2.0 molar portions of 1,5-diazabicyclo[5.4.0]undec-5-ene (DBU) (M. A. Nashed and L. Anderson, *J. Chem. Soc., Chem. Commun.*, (1982) 1274–1276). The product, by either method, is 2-pentadecyl-(3-O-benzyl-1,2 dideoxy-6-O-palmitoyl-α-D-glucopyrano)-[2,1-d]-2-oxazoline (compound 8').

The Compound 8' is phosphorylated to Compound 9'. For phosphorylation by the method of R. L. Letsinger and W. B. Lunsford, *J. Am. Chem. Soc.*, 98 (1976) 3655–3661, Compound 8' is added to a mixture of 2,2,2-trichloroethyl phosphorodichloridite and 2,6-dimethylpyridine in tetrahydrofuran at $-30°$ C. The reaction mixture is treated next with 2,2,2-trichloroethanol, then iodine-2,6-dimethylpyridine-tetrahydrofuran-water, to give 2-pentadecyl-[3-O-benzyl-4-O-(bis-2,2,2-trichloroethylphospho)-1,2-dideoxy-6-O-palmitoyl-α-D-glucopyrano]-[2,1-d]-2-oxazoline (Compound 9'), the fully developed precursor of the nonreducing half of the target disaccharides. Compound 9' is the analog of Compound 9 in FIG. 1. The bis(trichloroethyl)phospho group at position 4 in Compound 9' serves as its own protecting group during the coupling of Compound 9' and Compound 11b to yield Compound 12b' and the final palmitoylation steps to obtain Compound 15b. The two steps of the previous procedure which have been eliminated are the chloroacetylation and de-chloroacetylation reactions which converted Compound 7 to Compound 8 and Compound 13b to Compound 14b (as seen in FIG. 1). The deblocking of Compound 15b to the monodephosphopalmitoyl lipid A (17b) may be accomplished in a single step.

For the preparation of complete lipid A or an analog with two phosphate groups, the Compound 11a of FIG. 1 is coupled with 9' to give the allyl analog of 12b'. This is palmitoylated to 15a (second compound in FIG. 4), and the latter processed as in FIG. 4, or according to the literature.

In another embodiment the synthetic route is modified at the stage where Compound 5 is converted into 7. In the procedure of FIG. 1, Compound 5 is first selectively palmitoylated at position 6 (Compound 5 to Compound 6), then the aglyconic allyl group is isomerized to 1-propenyl (Compound 6 to Compound 7). We now have discovered that reversing the order of these two steps gives more reliable results.

The rearrangement of the allyl group in Compound 5 is catalyzed by tris(triphenylphosphine) rhodium(I) chloride in the manner described by E. J. Corey and J. W. Suggs, *J. Org. Chem.*, 38 (1973) 3224 and P. A. Gent and R. Gigg, *J. Chem. Soc., Chem Commun.*, (1974) 277–278 to provide 1-propenyl 3-O-benzyl-2-deoxy-2-palmitamido-β-D-glucopyranoside (Compound 6', not shown). The treatment of that compound with 1.5 molar portions of palmitoyl chloride in pyridine at $-10°$ C. effects selective acylation of the primary hydroxyl, and gives 1-propenyl 3-O-benzyl-2-deoxy-2-palmitamido-6-O-palmitoyl-β-D-glucopyranoside (Compound 7).

When analogs of 1-dephospho lipid A are desired (see FIG. 2), the preferred precursor of the reducing half of the molecule is benzyl 2-deoxy-2-palmitamido-3-O-palmitoyl-β-D-glucopyranoside (Compound 11b). For the preparation of complete analogs (phosphate groups at positions 1 and 4', see FIG. 3), it is better to use 1-propenyl 2-deoxy-2-palmitamido-3-β-O-palmitoyl-β-D-glucopyranoside (Compound 11c). Compound 11c is prepared from Compound 11a by the method, detailed above, used for the conversion of Compound 5 into Compound 6'.

The coupling of the oxazoline 9' to acceptors of Formula III is preferably conducted in 1,2-dichloroethane at 70° C. The preferred catalyst is 2,6-dimethylpyridinium p-toluenesulfonate, described by R. Gigg and R. Conant, *Carbohydr. Res.*, 100 (1982) C1–C4. Under these conditions the coupling of Compound 9' to 11b and 11c gives the phosphorylated disaccharides 12b' and 12c', respectively, in good yields.

On treatment with palmitoyl chloride Compounds 12b' and 12c' undergo palmitoylation at position 4 to give the fully substituted disaccharides 15b ($R_7=R_8=$2,2,2-trichloroethyl) and 15c (see below).

Removal of the protecting groups (trichloroethyl, benzyl) from Compound 15b (15b→16b→17b, FIG. 4; see also FIG. 2 of drawing) will furnish an analog of 1-dephospho lipid A (Compound 17b).

A route for the conversion of Compound 15c to a complete analog of lipid A is shown below. This route is based on Inage et al., *Tetrahedron Lett.*, 22 (1981) 2281–2284, and van Boeckel et al., *Tetrahedron Lett.*, 23 (1982) 1951–1954.

The key intermediates 5 and 11a and 11b may be prepared from allyl and benzyl 2-deoxy-2-palmitamido-β-D-glucopyranosides (Compounds 2a and 2b) via the 4,6-O-benzylidene derivatives 3a and 3b as indicated in the original application. However, we prefer the route shown below, proceeding via Compounds 3a' and 3b', in which positions 4 and 6 are protected by an isopropylidene rather than a benzylidene group. Compound 3b' was described by Kiso et al., *Carbohydr. Res.* 90 (1981) C8–C11. In their communication on the synthesis of lipid A analogs, van Boeckel et al., *Tetrahedron Lett.* 23 (1982) 1951–1954 mention, but do not fully describe, intermediates 3a', 4', and 10a'. Compound 10b' can be prepared by the palmitoylation of 3b' by the procedure used to convert Compound 3b into 10b.

The following examples further illustrate the modified procedure:

EXAMPLE 18

1-Propenyl 3-O-benzyl-2-deoxy-2-palmitamido-β-D-glucopyranoside (6')

To a solution of Compound 5 (3.2 g., 5.84 mmol) in ethanol:benzene:water (7:3:1, v/v) (250 ml.) were added diazabicyclo[2.2.2]octane (0.2 g, 1.8 mmol) and tris(triphenylphosphine) rhodium(I) chloride (0.4 g., 0.43 mmol). The mixture was stirred for 24 h. under reflux. Solvents were evaporated and coevaporated with toluene. A portion of the product, purified on a column of silica gel, afforded an amorphous solid, $[\alpha]_D^{25} -7.4°$, $[\alpha]_{436}^{25} -13/3°$ (chloroform).

EXAMPLE 19

1-Propenyl 3-O-benzyl-2-deoxy-2-palmitamido-6-O-palmitoyl-β-D-glucopyranoside (7)

Compound 6' (6 g., 11.0 mmol) was dissolved in dry pyridine (120 ml.), and the solution was cooled at −10°. Palmitoyl chloride (4.7 ml., 16.8 mmol) was added dropwise while the reaction mixture was stirred at −10°. After an additional 30 min. the mixture was allowed to warm up to room temperature and then stirred for 2 h. The product was isolated by conventional chloroform extraction. After purification on a column of silica gel, the yield of 7 was 7.6 g (88%).

EXAMPLE 20

2-Pentadecyl-(3-O-benzyl-1,2-dideoxy-6-O-palmitoyl-α-D-glucopyrano)-[2,1-d]-2-oxazoline (8').

To pure 7 (300 mg., 0.38 mmol) in tetrahydrofuran (15 ml.), iodine (145 mg., 1.5 molar proportions) was added followed by 1,5-diazabicyclo[5.4.0]undec-5-ene (DBU) (114 mg., 2 molar proportions). The mixture was stirred for 5 min. at room temperature, chloroform was added, and the organic layer was washed successively with water, 5% sodium bisulfite, and water, and then dried over magnesium sulfate. After purification on a column of silica gel, the yield of 8' was 230 mg (83%), $[\alpha]_D^{25} -9.1$ (chloroform).

EXAMPLE 21

2-Pentadecyl-[3-O-benzyl-4-O-(bis-2,2,2-trichloroethylphospho)-1,2-dideoxy-6-O-palmitoyl-α-D-glucopyrano]-[2,1-d]-2-oxazoline (9').

To a solution of 2,2,2-trichloroethyl phosphorodichloridite (0.3 ml., 1.9 mmol) in tetrahydrofuran (20 ml.), 2,6-dimethylpyridine (1.2 ml., 10.3 mmol) was added at −30°. A heavy white precipitate formed during the addition. Compound 8' (1.0 g., 1.38 mmol) in tetrahydrofuran (10 ml.) was added dropwise with stirring while the mixture was maintained at −30°. After an additional 45 min, 2,2,2-trichoroethanol (0.26 ml., 2.71 mmol) was added dropwise and then the mixture was stirred at −30° for 45 min, and the vessel was removed from the cooling bath. When the temperature reached −10°, a solution of iodine (0.52 g., 2.05 mmol) and 2,6-dimethylpyridine (2 ml.) in tetrahydrofuran-water (2:1, v/v, 10 ml.) was added. The resulting solution was stirred as it warmed to room temperature, chloroform was added, and the organic layer was washed successively with water, freshly prepared 5% sodium bisulfite, and water, and then dried over anhydrous magnesium sulfate. Most of the high boiling substances were removed, prior to chromatography, on a liquid nitrogen trap under vacuum. After purification on a column of silica gel, the yield of 9' was 1.33 (91%), amorphous solid, $[\alpha]_D^{25} +17.9°$, $[\alpha]_{436}^{25} +31.9°$ (chloroform).

EXAMPLE 22

Benzyl O-[3-O-benzyl-4-O-(bis-2,2,2-trichloroethylphospho)-2-deoxy-2-palmitamido-6-O-palmitoyl-β-D-glucopyranosyl]-(1→6)-2-deoxy-2-palmitamido-3-O-palmitoyl-β-D-glucopyranoside (12b')

To a solution of Compound 11b (145 mg., 0.19 mmol) and 2,6-dimethylpyridinium p-toluenesulfonate (90 mg., 0.30 mmol) in dry 1,2-dichloroethane (2 ml.), the oxazoline derivative 9' (315 mg., 0.29 mmol) was added. The reaction mixture was stirred at 70° for 40 h under anhydrous conditions, then chloroform was added and the organic layer was washed with water. Evaporation of the solvents gave a dried syrup that was purified on a column of silica gel. The yield of 12b' was 220 mg. (62%), wax, $[\alpha]_D^{25} -2.1°$ (chloroform).

EXAMPLE 23

Benzyl O-[3-O-benzyl-4-O-(bis-2,2,2-trichloroethylphospho)-2-deoxy-2-palmitamido-6-O-palmitoyl-β-D-glucopyranosyl]-(1→6)-2-deoxy-2-palmitamido-3,4-di-O-palmitoyl-β-D-glucopyranoside (15b).

To Compound 12b' (45 mg., 24 μmol) in tetrahydrofuran (2 ml.) and pyridine (0.5 ml.), palmitoyl chloride (0.17 ml.) was added and then the reaction mixture was stirred at room temperature overnight. The product was isolated by conventional chloroform extraction, then the residue obtained was purified on a column of silica gel. This gave 44 mg (86%) of the title compound, amorphous solid; $[\alpha]_D^{25} +18.3°$, $[\alpha_{436}^{25} +36.7$ (chloroform).

EXAMPLE 24

1-Propenyl 2-deoxy-2-palmitamido-3-O-palmitoyl-β-D-glucopyranoside (11c).

To a solution of Compound 11a (100 mg.) in ethanol:-benzene:water (7:3:1, v/v) (15 ml.), were added diazabicyclo [2 2 2]-octane (15 mg.) and tris(triphenylphosphine)rhodium(I) chloride (40 mg.). The mixture was stirred for 24 h under reflux. Solid material was filtered off and the filtrate was evaporated and co-evaporated with toluene. The residue, purified by chromatography on a column of silica gel, yielded 90 mg. of pure 11c.

EXAMPLE 25

1-Propenyl O-[3-O-benzyl-4-O-(bis-2,2,2-trichloroethylphospho)-2-deoxy-2-palmitamido-6-O-palmitoyl-β-D-glucopyranosyl]-(1→6)-2-deoxy-2-palmitamido-3-O-palmitoyl-β-D-glucopyranoside (12c').

To a solution of compound 11c (20 mg.) and 2,6-dimethylpyridinium p-toluenesulfonate (10 mg.) in dry 1,2-dichloroethane (0.2 ml.), the oxazoline derivative 9' (40 mg.) was added. The reaction mixture was stirred at 70° for 24 h under anhydrous conditions, then chloroform was added and the organic layer was washed with water, 5% sodium hydrogen carbonate, and water. Evaporation of the solvents left a syrup that was then purified on a column of silica gel. The yield of the waxy title compound was 24 mg.

As previously indicated lipid A and its analogs are of considerable biochemical and pharmacological interest. Recent publications reporting the results of tests indicating that lipid A is a component of preparations having anti-tumor activity are the following:

E.E. Ribi, D. L. Granger, K. C. Millner, and S. M. Strain, Journal of the National Cancer Institute, 55 (1975) 1253-7 "Tumor Regression Caused by Endotoxins and Mycobacterial Fractions."

E. Ribi, K. Takayama, K. Milner, G. R. Gray, M. Goren, R. Parker, Ch. McLaughlin, and M. Kelly, Cancer Imjunology and Immunotherapy, 1 (1976) 265-70 "Regression of Tumors by an Endotoxin Combined with Trehalose Mycolates of Differing Structure."

E. Ribi, R. Parker, S.M. Strain, Y. Mizuno, A. Nowotny, K. B. Von Eschen, J. L. Cantrell, C. A. McLaughlin, K. M. Hwang and M. B. Goren, Cancer Immunology and Imjunothrapy, 7 (1979) 43-58 "Peptides as Requirement for Immunotherapy of the Guinea-pig Line-10 Tumor with Endotoxins."

K. Takayama, E. Ribi, K. Von Eschen, and G. Stein, Abstracts of the Annual Meeting of the American Society for Microbiology, 80th Annual Meeting, Miami Beach, Fla., May 11-16, 1980 "Relating Structural Variation of Endotoxin from the Rough Mutant of Salmonella Typhimurium to Anti-Tumor Activity and Toxicity."

E. Ribi, J. L. Cantrell, S. M. Schwartzman, R. Parker and K. Takayama, 15th Joint Research Conference on Tuberculosis, Gakushi-Kaikan, Tokyo, Oct. 6-8, 1980, 347-57 "Structure and Function Relationships Between Mycobacterial Components and Endotoxic Extracts from Gram-Negative Re Mutant Bacteria."

It will be readily apparent to those skilled in the art that the precursors of Formula II and Formula III may be coupled using other catalysts and conditions than those described in the examples. For example, in place of 1,2-dichloroethane other solvents for the p-toluenesulfonic acid-catalyzed coupling may be used. See S. E. Zurabyan, T. P. Volosyuk, and A. J. Khorlin, Carbohydr. Res., 9 (1969) 215-220; S. David and A. Veyrieres, Carbohydr. Res., 40 (1975) 23-29; and R. Kaifu, T. Osawa, and R. W. Jeanloz, Carbohydr. Res., 40 (1975) 111-117. In addition, ferric chloride might be used as the catalyst instead of p-toluenesulfonic acid. M. Kiso and L. Anderson, Carbohydr. Res., 72 (1979) C15-C17.

It will be apparent to those skilled in the art that a number of further modifications and changes may be made without departing from the spirit and scope of the present invention. For example, s:nce in place of benzyl in the compounds of the examples substituted benzyl groups such as methoxybenzyl, halobenzyls and the like may be used provided they do not interfere with or partake in the reactions, the term "benzyl" as used herein is to be interpreted as including such substituted benzyls. Furthermore, the term "hydroxyalkyl" as used herein is intended to cover not only hydroxyalkyl compounds but also protected hydroxy alkyl compounds in which the hydroxy group is protected with one of the protective groups described by McOmie in pages 96 to 135 in his text "Protective Groups in Organic Chemistry", Plenum Press, 1973 which is incorporated by reference herein. Therefore, it is intended that the invention is not to be limited except by the claims which follow:

We claim:

1. A method of preparing a disaccharide of the formula:

in which R is an alkyl, hydroxyalkyl or protected hydroxyalkyl group of 7 to 19 carbon atoms; $R_1$ is selected from allyl, benzyl, 1-propenyl, or trichloroethyl; $R_3'$ is selected from allyl, crotyl, 2-methoxyethoxymethyl, methylthiomethyl, or benzyl; $R_4'$ is hydrogen, chloroacetyl, or β-benzoylpropionyl; and $R_4$ is hydrogen or said method comprising reacting a compound of the formula:

with a compound of the formula:

in which all symbols are as previously defined, in the presence of a coupling catalyst selected from p-toluenesulfonic acid and 2,6-dimethylpyridinium p-toluenesulfonate.

2. The method of claim 1 in which R is an alkyl of 15 carbon atoms.

3. The method of claim 1 in which $R_3'$ is benzyl.

4. The method of claim 1 in which $R_4$ is hydrogen.

* * * * *